US 8,797,660 B1

(12) United States Patent
Mansfield et al.

(10) Patent No.: US 8,797,660 B1
(45) Date of Patent: Aug. 5, 2014

(54) ALIGNMENT MECHANISM FOR PHOTOELASTIC MODULATORS

(71) Applicant: Hinds Instruments, Inc., Hillsboro, OR (US)

(72) Inventors: James C. Mansfield, Tigard, OR (US); Hugh S. Runyan, Portland, OR (US); Jacob A. Wolf, Portland, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 33 days.

(21) Appl. No.: 13/720,928

(22) Filed: Jan. 23, 2013

(51) Int. Cl.
*G02B 7/02* (2006.01)
*G02B 7/00* (2006.01)
*G02B 7/182* (2006.01)
*G02B 27/28* (2006.01)
*G01N 21/01* (2006.01)

(52) U.S. Cl.
CPC .............. *G02B 7/006* (2013.01); *G02B 7/1822* (2013.01); *G02B 7/1825* (2013.01); *G02B 27/28* (2013.01); *G01N 21/01* (2013.01); *G01N 2201/0224* (2013.01)
USPC ......................................... 359/811; 359/819

(58) Field of Classification Search
CPC ........ G02B 7/003; G02B 7/004; G02B 7/006; G02B 7/182; G02B 7/1822; G02B 7/1824; G02B 7/1825; G02B 27/28; G01N 21/01
USPC .................... 356/244, 365; 359/811, 813, 819
See application file for complete search history.

(56) References Cited

U.S. PATENT DOCUMENTS

| 6,765,734 B1 | 7/2004 | Griffiths |
| 6,906,844 B1 | 6/2005 | Siahpoushan |
| 7,580,207 B2 * | 8/2009 | Melzer .......................... 359/822 |
| 7,800,845 B2 * | 9/2010 | Mansfield ..................... 359/811 |
| 8,537,476 B2 * | 9/2013 | Mansfield et al. ............ 359/811 |
| 2008/0001055 A1 | 1/2008 | Mansfield |
| 2008/0174773 A1 | 7/2008 | Mark |

FOREIGN PATENT DOCUMENTS

| WO | 9917098 | 4/1999 |
| WO | 2009148455 | 12/2009 |

OTHER PUBLICATIONS

Images of a prior art barrel, grommet and conical member used to support an optical element; Hinds Instruments, Dec. 2000.
Hinds Instruments Catalog Excerpt; 3 pages; Jan. 2007.

* cited by examiner

*Primary Examiner* — David N Spector
(74) *Attorney, Agent, or Firm* — Hancock Hughey LLP

(57) ABSTRACT

A mechanism and method for precisely arranging two or more optical elements, such as those incorporated into photoelastic modulators (PEMs), at a specific angular orientation. The method includes supporting one optical element in an annular mounting member that has an optic axis, and supporting other optical elements in other annular mounting members that have optic axes, and concentrically stacking together the two or more mounting members about a central axis in a manner such that one mounting member may be rotated relative to the others about the central axis and such that the optic axes of the mounting members define an optics angle, and rotating one mounting member relative to the others to define the specific angular orientation of the optical elements.

19 Claims, 3 Drawing Sheets

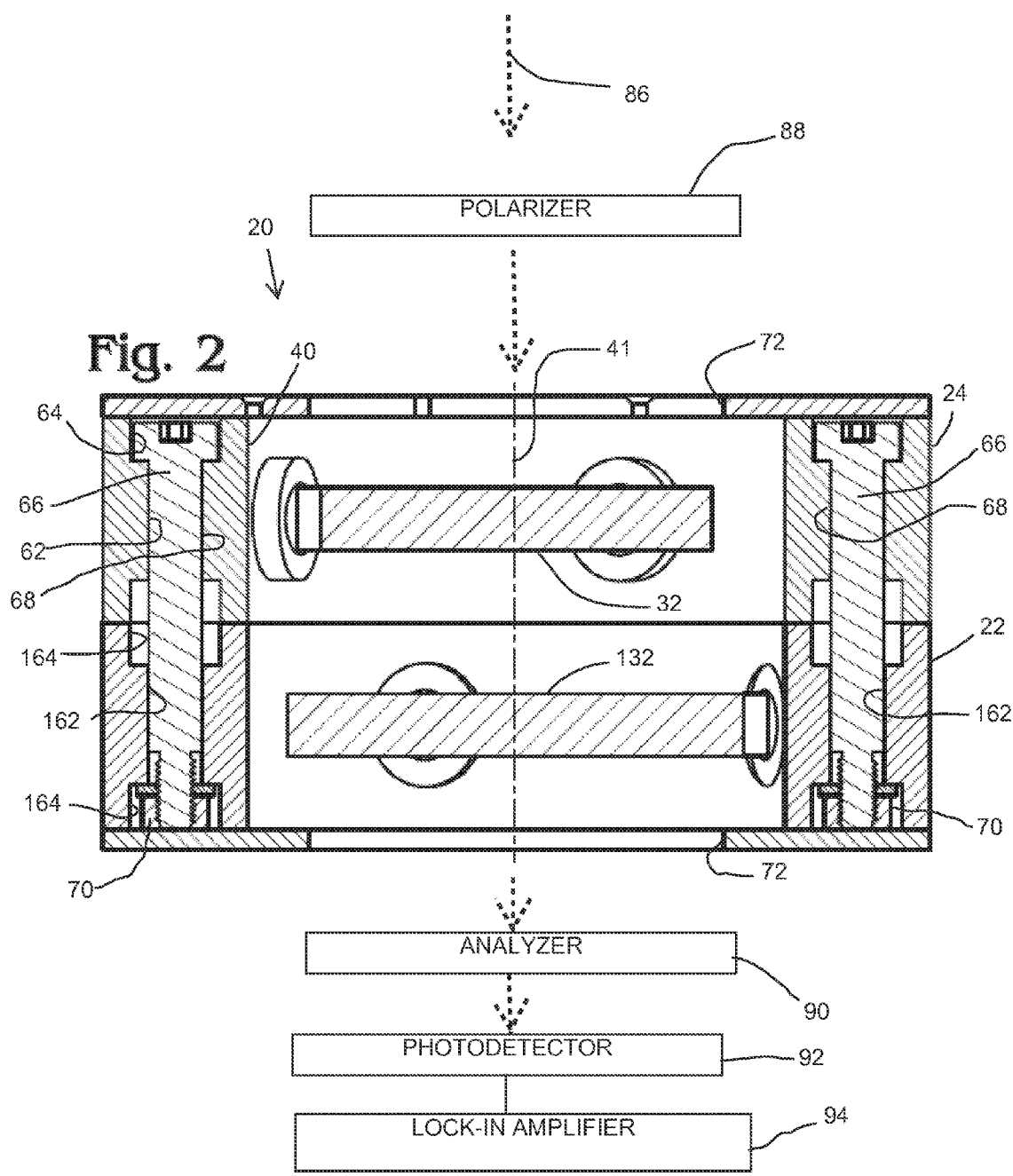

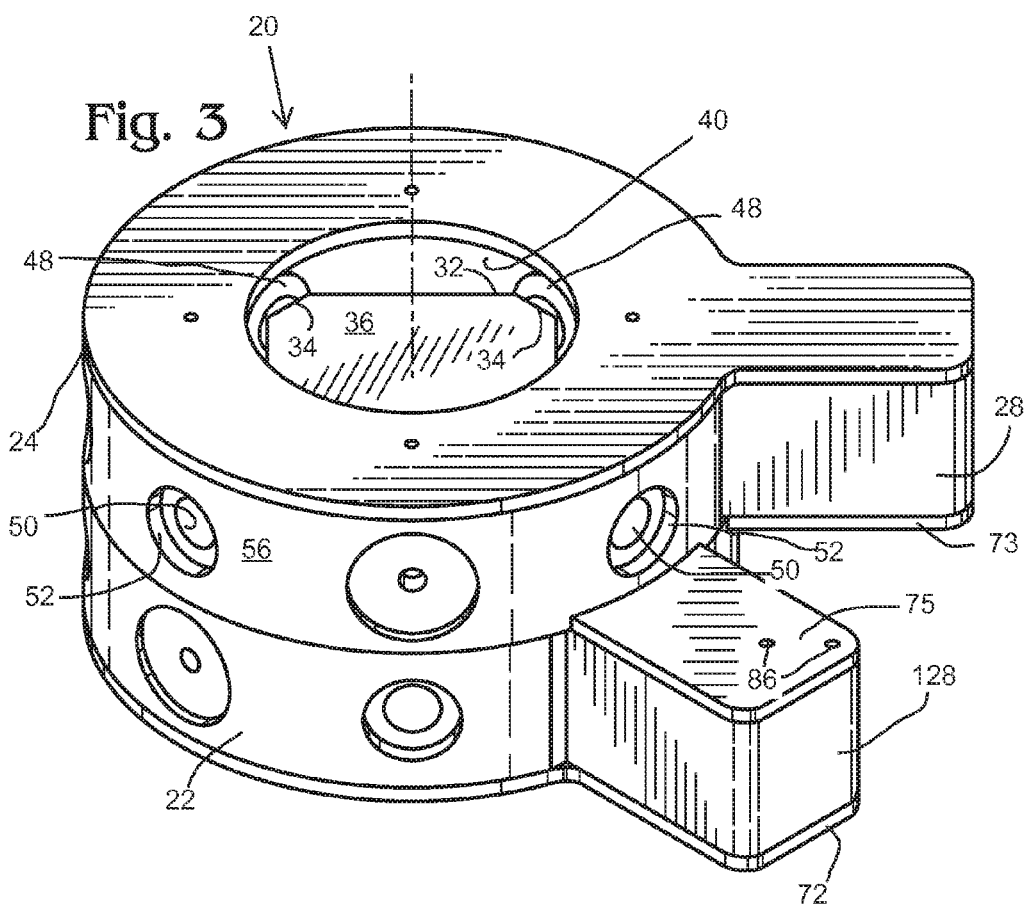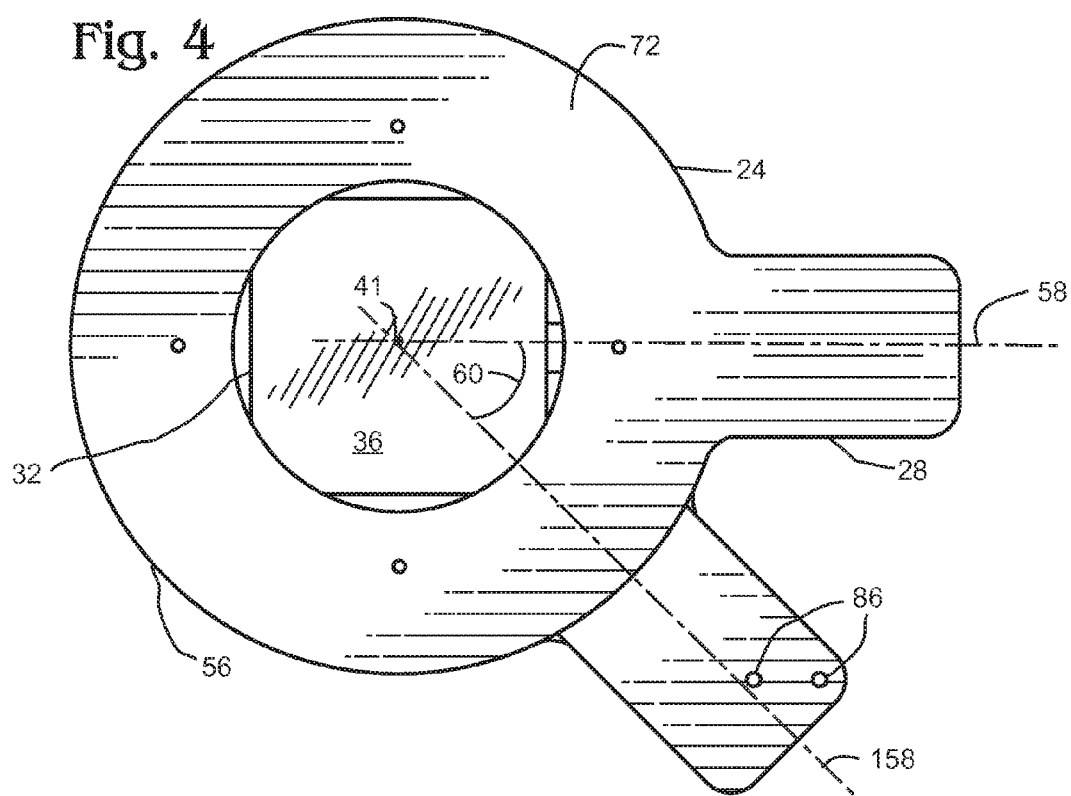

ALIGNMENT MECHANISM FOR PHOTOELASTIC MODULATORS

TECHNICAL FIELD

This application relates to a mechanism and method for precisely arranging the optical axes of two or more optical elements, such as those incorporated into photoelastic modulators, in a selected angular orientation.

BACKGROUND

A photoelastic modulator (PEM) is an instrument that is used for modulating the polarization of a beam of light. A PEM employs the photoelastic effect as a principle of operation. The term "photoelastic effect" means that an optical element that is mechanically stressed and strained (deformed) exhibits birefringence that is proportional to the amount of deformation induced into the element. Birefringence means that the refractive index of the optical element is different for different components of a beam of polarized light.

A PEM includes an optical element, such as fused silica, that has attached to it a transducer for vibrating the optical element. The transducer vibrates at a fixed frequency within, for example, the low-frequency, ultrasound range of about 20 kHz to 100 kHz. The mass of the element is compressed and extended along the axis of the optical element as a result of the vibration. The combination of the optical element and the attached transducer may be referred to as an optical assembly. The axis about which the optical element vibrates is referred to as the optical axis of the PEM.

The optical assembly is mounted within a housing or enclosure that normally includes an aperture through which the light under study is directed through the optical element in a direction generally perpendicular to the optical axis of the PEM. The enclosure supports the optical assembly in a manner that permits the optical element to be driven (vibrated) within it to achieve the above-noted photoelastic effect.

PEMs are commonly used in measuring polarization properties of either a light beam or a sample. Many instruments use two or more PEMs to provide measurements of certain polarization properties. When two PEMs are used in a single instrument, they are typically arranged so that their optical axes are oriented to be precisely 45 degrees apart (as considered in a direction perpendicular to those two optical axes).

Examples of typical, two-PEM instruments include complete Stokes polarimeters, Tokomak polarimeters, and a number of other polarimeters and ellipsometers. When four PEMs are used in one instrument, the PEMs are typically grouped in separate pairs.

The speed and precision with which a pair of PEMs can be oriented so that their optical axes are fixed at a particular, selected angle depends greatly on the precision with which the housing or enclosure to which the PEMs are mounted can be positioned and secured to place the PEMs in that proper orientation.

SUMMARY OF THE INVENTION

The present invention is directed to a mechanism and method for precisely arranging two or more optical elements, such as those incorporated into PEMs, at a specific angular orientation.

BRIEF DESCRIPTION OF THE DRAWINGS

FIG. 2 is a cross sectional view of the mechanism taken along line 2-2 of FIG. 1.

FIG. 3 is a perspective view of the mechanism of FIG. 1 with the cover replaced and the actuator removed.

FIG. 4 is a top plan view of FIG. 3.

DETAILED DESCRIPTION

Figure 1:
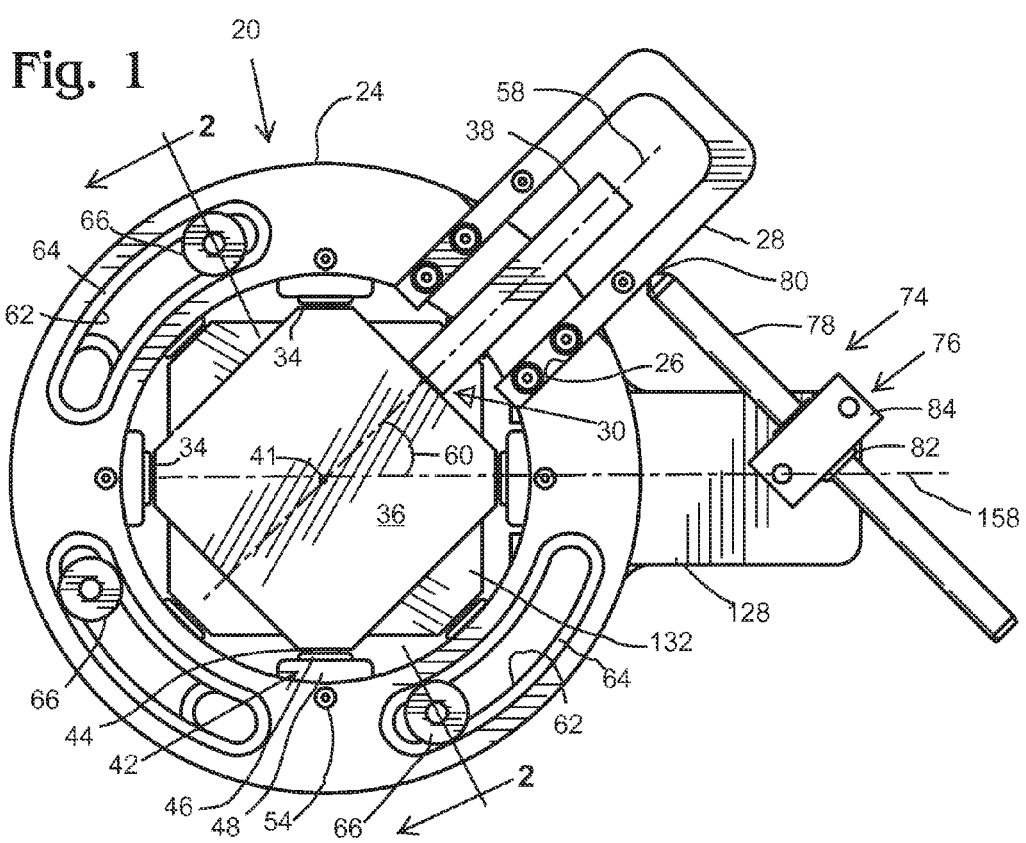
FIG. 1 is a top plan view of a mechanism formed in accordance with the present invention, with a cover removed and with an actuator connected thereto for adjusting the mechanism.

One embodiment of a mechanism 20 formed in accordance with the present invention is depicted in the figures. The mechanism 20 includes two generally annular mounting members, hereafter referred to as a lower mounting member 22 and upper mounting member 24. The designation of "lower" and "upper" is for reference purposes only. The mounting members 22, 24 are nearly identical in construction and are interchangeable. The following description focuses on the upper mounting member 24 with the understanding that the lower mounting member 22 is similarly constructed except where otherwise specified.

The upper mounting member 24 is metal and is generally annular with a depth (measured vertically in FIG. 2) that is about one-half of its radius (as measured in a plan view). A notch 26 (FIG. 1) is cut through the mounting member 24. An open end of a somewhat elongated enclosure 28 is attached to the mounting member at the notch 26 to protrude radially outwardly therefrom. (The corresponding enclosure of the lower mounting member 22 is shown at 128.) It is noteworthy that the mounting member may also be formed of rigid plastic, such as Delrin®. This would be a useful configuration when the mechanism is used in a magnetic field as occurs, for example, in Tokomak polarimeter applications.

A primary function of each mounting member 22, 24 is to support the optical assembly of a photoelastic modulator (PEM) 30. The primary components of the PEM's optical assembly include an optical element 32 formed of fused silica. Other material, such as fused quartz, calcium fluoride, zinc selenide, silicon and others may be used to form the optical element. (The corresponding optical element supported in the lower mounting member 22 is shown at 132.)

The optical element 32 is a generally square-shaped member but having beveled corners that define flat support surfaces 34, the function of which is described below. The optical element also has an entry surface 36 against which an incident light beam is directed while the PEM is operating. A quartz piezoelectric transducer 38 (FIG. 1) is bonded to one of the four sides of the optical element 32. Electrical leads (not shown) from the transducer are connected to a driver circuit for vibrating the optical element 32.

The optical element 32 is supported so that its entry surface 36 extends across the central aperture 40 of the upper mounting member 24. Preferably, the center of the entry surface is aligned with the central axis 41 of that aperture 40 (FIGS. 2 and 3). The optical element 32 is free to vibrate when driven as described above. In this regard, the optical element 32 is mounted to the upper mounting member 24 by somewhat flexible supports 42 (FIG. 1) that secure the optical element 32 at each support surface 34 so that the optical element is substantially suspended within the central aperture 40 of the upper mounting member 24.

Each one of the supports 42 includes an elastomeric rod 44 that may be formed, for example, from extruded silicone (polysiloxane) cords that are cut to a specified length to define the rod 44. One of the two, flat ends of the rod 44 is attached, as by an adhesive, to one of the support surfaces 34 on the optical element 32.

The other, free end of the rod 44 fits within a sleeve 46 that is carried inside of a cylindrical slider 48. The sleeve 46 has a cylindrical axial bore formed through one end to receive the elastomeric rod 44. The sleeve 46 is a rigid, externally threaded member that is threaded into an internally threaded bore 50 (FIG. 3) of the slider 48.

Each on of the four sliders 48 fits inside of a radial hole 52 (FIG. 3) formed through the curved side 56 of the upper mounting member 24. The slider 48, with the sleeve 46 threaded into its bore 50, is slid with the radial hole 52 until the rod 44 is received in the bore of the sleeve 46. The slider 48 is secured in place via a setscrew 54 that is threaded vertically (FIG. 1) through the upper mounting member 24 to bear against the slider.

With the slider secured in place, the sleeve 46 is advanced until the free end of the rod 44 (that is, the end not bonded to the optical element support surface 34) is completely received within the bore of the sleeve. The sleeve 46 may be advanced by hand or with a tool. In this regard, the outer end of the sleeve 46 may be shaped to define a socket for an Allen-type wrench or the like that can be extended into the bore 50 of the slider to reach the socket in the sleeve 46.

The foregoing description of an exemplary support 42 applies to all four supports 42 on both mounting members 22, 24. As depicted in FIG. 1, four supports are employed to secure the optical element 32 in place relative to the upper mounting member 24. The supports are thus arranged in diametrically opposed pairs. Alternative configurations of such supports 42 are contemplated, such as those described in U.S. Pat. No. 7,800,845 owned by the assignee of this application. As another alternative, the rod 44 could be replaced with a glass or plastic conical member with the base of the cone bonded to the support surface 34 and the pointed end seated in the central opening of an annular elastomeric grommet that is mounted on the end of a cylindrical barrel that is secured in the hole 52. In the figures, the grommet and barrel would appear as the sleeve 46 and slider 48 respectively. The setscrew 54 would hold the barrel and grommet combination in place.

The transducer 38 is attached to the optical element 32, and not otherwise supported by the upper mounting member 24. The transducer 38 is an elongated, bar-like member that extends from the optical element 32 and into the enclosure 28 that protrudes radially outwardly from the outer, curved surface 56 of the upper mounting member 24. The longitudinal axis 58 of the transducer 38 is aligned with the center of the optical element 32 and, as such, this axis 58 coincides with the optical axis of that optical element.

For purposes of this description, the projection of the optical axis of the optical element 32 of the PEM 30 onto the structure of the upper mounting member 24 is illustrated by axis line 58, which will hereafter be referred to as the optics axis 58 of the upper mounting member 24. The lower mounting member 22 has a similarly defined optic axis 158, as shown in FIGS. 1, 3 and 4.

The angle between these two optics axes 58, 158 (as viewed along the central axis 41 (see FIGS. 1 and 4) is referred to as the optics angle 60. It will be appreciated that the optics angle 60 (and the associated adjustments to that angle discussed below) corresponds directly to the angle between the optical axis of the optical element 32 in the upper mounting member 24 and the optical axis of the optical element 132 in the lower mounting member 22. Any minor variations between those two axes (which may be attributable to, for example, a slight misalignment of the supports 42 that secure the optical elements 32, 132 in place) can be accounted for as will be discussed below.

As best shown in FIGS. 1 and 2, each mounting member 22, 24, includes three, spaced-apart, elongated guide slots 62, 162 that, in plan view, are curved about the central axis 41. The guide slots 62, 162 are counterbored into the opposite flat surfaces of the upper and lower mounting members 22, 24. The counterbored portions 64, 164 of the guide slots thus provide recesses within which the opposite ends of shoulder bolts 66 are received.

As shown in the figures, the upper mounting member 24 and lower mounting member 22 are stacked together, concentric with the central axis 41. The guide slots 62, 162 are precisely, concentrically aligned so that the smooth, shoulder portion 68 of each shoulder bolt 66 fits vertically through the stacked mounting members (See FIG. 2) to serve as guide pins so that one mounting member can be precisely rotated relative to the other about the central axis 41. The head of each shoulder bolt 66 fits inside a counterbored portion 64. The threaded end of the bolt, to which a flanged nut 70 is fastened, also fits inside of a counterbored portion 164 of the guide slots. The nuts 70 are sized so that they will not rotate with the bolt 66. When the precise, desired optics angle 60 is established, the shoulder bolts 66 are tightened (as by an Allen wrench applied to the hex socket in the bolt head) to lock the upper mounting member 24 to the lower mounting member 22, thereby fixing the optics angle.

In a preferred embodiment, the upper and lower flat surfaces of the stacked upper mounting member 24 and lower mounting member 22 are provided with thin cover plates 72, the uppermost plate being added after the bolts 66 are all tightened. The underside of the radially protruding portion of the enclosure 28 of the upper mounting member 24 has a cover plate 73, and the upper side of the radially protruding portion of the enclosure 128 of the lower mounting member 22 has a cover plate 75 (FIG. 3).

It is contemplated that once the upper and lower mounting members 24, 22 are stacked but not rotatably fixed together by bolts 66, any one of a variety of actuators may be employed for precisely rotating one mounting member relative to the other until the desired optics angle 60 is established. The actuator may be applied to any part of one mounting member to force rotation of that mounting member relative to the other. The actuator can be connected to a work surface adjacent to the rotated mounting member. Alternatively, the actuator can be connected to one mounting member (which member is secured to be stationary) and operable to apply force to the other mounting member. The actuator may be a permanent component of the overall mechanism, or be configured for removal once the precise optics angle is established, and the mounting members locked together. The actuator can be manually operated or mechanically driven under computer control.

In a preferred embodiment, an actuator 74 (FIG. 1) for providing precise rotation of one mounting member relative to the other comprises a fine adjustment screw assembly 76. That assembly includes and elongated screw 78, one end of which 80 is rounded and engages an exterior surface of the enclosure 28 that protrudes radially from the upper mounting member 24 (FIG. 1). The screw 78 is threaded through a bushing 82 that is mounted within a base 84 of the assembly. The base 84 (hence the assembly) is connected to the cover plate 75 of the lower mounting member enclosure 128 via fasteners that are threaded into mounting holes 86 (FIG. 4). Rotation of the ultra fine pitched screw is transferred via the contact of end 80 with the enclosure 28 into rotation of the upper mounting member 24 relative to the lower mounting member 22, which member 22 may or may not be secured in place while this adjustment is made.

As noted above, the angle between the two optics axes 58, 158 (namely; the optics angle 60) that is adjusted as just described corresponds directly to the angle between the optical axes of the optical elements 32, 132 in the respective upper mounting member 24 and lower mounting member 22. Any minor variations between one optic axis 58, 158 and the corresponding optical axis of the associated optical elements 32, 132 (which variations may be attributable to, for example, a slight misalignment of the supports 42 securing the optical elements 32, 132 in place) can be addressed while the mechanism 20 is located in an optical setup with light passing though the optical elements of both PEMs and detected. This approach can be referred to as the PEMs optical angle calibration.

One approach to this calibration is schematically depicted in FIG. 2, where the mechanism 20 is part of a setup that includes a light source 86, adjustable polarizer 88, an adjustable analyzer 90, photodetector 92 and an associated lock-in amplifier 94. The procedure discussed next is for precisely establishing the angle between the optical axes of the two PEMs to be 45°, although other angles may be selected.

The polarizer 88 is set at 0° and the analyzer 90 is set at 45°. The upper mounting member 24 is rotated as described above until the optics axis 60 is at 45°. This angle can be measured in any of a number of ways, including the use of angular graduations on the exposed, adjacent surfaces of the mounting members. Next, the PEM 30 in the upper mounting member 24 is operated at a peak retardation of one-half wave while the PEM in the lower mounting member 22 remains off. The 2F signal on the detector 92 is monitored using the lock-in amplifier 94. The mechanism 20 is then employed to precisely rotate the upper mounting member 24 relative to the lower mounting member 22 until the 2F signal reads "0," at which point the upper mounting member 24 and lower mounting member 22 are locked together using the shoulder bolts 66 as described above.

While the foregoing description was made in the context of a preferred embodiment, it is contemplated that modifications to the embodiment may be made without departure from the invention as claimed. For example, it is contemplated that the preferred embodiment of the actuator 74 may include the application of a spring or latch member extending between the adjustment screw and enclosure 28 so that the enclosure will move with both the extension and retraction of the adjustment screw 78. Further, the actuator may be configured to act on any portion of the mounting members to impart the relative rotation, such portions can be considered protrusions but need not be the radially protruding enclosures discussed above.

The invention claimed is:

1. A mechanism for precisely arranging two optical elements, comprising:
    an annular first mounting member having a first optic axis and a first protrusion, the first mounting member including supports configured for supporting an optical element to extend across a central aperture in the first mounting member;
    an annular second mounting member having a second optic axis and a second protrusion, the second mounting member including supports configured for supporting an optical element to extend across a central aperture in the second mounting member;
    wherein the first and second mounting members are concentrically stacked together about a central axis with the first and second optic axes defining between them an optics angle;
    guide slots formed in each of the first and second mounting members;
    guide pins extending through the guide slots and configured for selectively permitting and preventing rotational motion between the first and second mounting members about the central axis; and
    an actuator located near the first mounting member and operable for rotating the first mounting member for varying the size of the optics angle.

2. The mechanism of claim 1 wherein the guide pins include threaded features operable for clamping together the stacked first and second mounting members, thereby preventing rotational motion between the first and second mounting members.

3. The mechanism of claim 1 wherein the actuator is removably located near the first mounting member and operable for applying force to the first protrusion to rotate the first mounting member.

4. The mechanism of claim 1 wherein the actuator includes a fine adjustment screw, one end of which engages the first protrusion.

5. The mechanism of claim 4 wherein the actuator also includes a base that is connectable to the second mounting member, and a bushing mounted to the base and through which bushing the adjustment screw is threaded for extension toward the first protrusion.

6. The mechanism of claim 1 wherein the guide slots are elongated and curved about the central axis.

7. The mechanism of claim 1 wherein the first and second mounting members have substantially planar outer surfaces that stack together and wherein the guide slots are counter-bored into the planar outer surfaces.

8. The mechanism of claim 7 wherein the guide pins comprise shoulder bolts, the opposite ends of the shoulder bolts each being received in a counterbored portion of one of the guide slots.

9. The mechanism of claim 1 wherein the first mounting member is rotatable relative to the second mounting member in instances when the guide pins are configured to permit such rotation, and wherein the supports are configured for connecting optical elements directly to the first and second rotatable mounting members so that the first and second mounting members serve the dual purpose of supporting an optical element while permitting relative rotation between the supported optical elements.

10. The mechanism of claim 1 wherein the first and second protrusions are each shaped to define an enclosure for receiving a component that may be attached to an optical element to extend from the optical element.

11. A method of concentrically mounting first and second optical elements with a selected angle between them, comprising the steps of:
    supporting the first optical element in an annular first mounting member that has a first optic axis;
    supporting the second optical element in an annular second mounting member that has a second optic axis;
    concentrically stacking together the first and second mounting members about a central axis in a manner such that one mounting member may be rotated relative to the other about the central axis and so that the optic axes of the first and second mounting members define between them an optics angle; and
    rotating one mounting member relative to another to define a selected angle between the first and second optical elements.

12. The method of claim 11 including after the rotating step the step of clamping together the first and second mounting members, thereby preventing further rotational motion between the first and second mounting members.

13. The method of claim 11 wherein the rotating step includes using an actuator to move apart radially protruding portions of the respective first and second mounting members.

14. The method of claim 13 including the step of connecting a fine screw adjustment to one of the first and second mounting members for extending between and moving apart the protruding portions of the respective first and second mounting members.

15. The method of claim 14 including after the rotating step the steps of clamping together the first and second mounting members and disconnecting the fine screw adjustment from the one of the first and second mounting members.

16. The method of claim 11 wherein the rotating step includes moving apart protruding portions of the respective first and second mounting members using an actuator and including after the rotating step the step of clamping together the first and second mounting members, thereby preventing further rotational motion between the first and second mounting members.

17. The method of claim 11 wherein the stacking step includes pinning together the first and second mounting members using pins that are received in curved guide slots formed in the first and second mounting members.

18. The method of claim 17 including the step of recessing the opposite ends of the pins within the respective first and second mounting members.

19. The method of claim 11 including the step of attaching to each of the first and second mounting members a protrusion that is shaped to define an enclosure for receiving a component that may be attached to extend from an optical element.

\* \* \* \* \*